(12) United States Patent
Wagner et al.

(10) Patent No.: US 9,381,021 B2
(45) Date of Patent: Jul. 5, 2016

(54) METHOD AND APPARATUS FOR FORMING A HOLE IN BONE DURING A SURGICAL PROCEDURE

(75) Inventors: Zachary Wagner, Lafayette, IN (US); Kevin T. Stone, Winona Lake, IN (US); Brian K. Berelsman, Warsaw, IN (US)

(73) Assignee: BIOMET SPORTS MEDICINE, LLC, Warsaw, IN (US)

( * ) Notice: Subject to any disclaimer, the term of this patent is extended or adjusted under 35 U.S.C. 154(b) by 712 days.

(21) Appl. No.: 13/242,157

(22) Filed: Sep. 23, 2011

(65) Prior Publication Data

US 2013/0079780 A1    Mar. 28, 2013

(51) Int. Cl.
*A61B 17/00* (2006.01)
*A61B 17/16* (2006.01)
*A61B 17/17* (2006.01)
*A61B 17/04* (2006.01)
*A61B 17/88* (2006.01)

(52) U.S. Cl.
CPC .......... *A61B 17/1615* (2013.01); *A61B 17/1675* (2013.01); *A61B 17/1714* (2013.01); *A61B 17/0401* (2013.01); *A61B 17/162* (2013.01); *A61B 17/1697* (2013.01); *A61B 17/8897* (2013.01); *A61B 2017/0404* (2013.01); *A61B 2017/0414* (2013.01)

(58) Field of Classification Search
CPC ........... A61B 17/1615; A61B 17/1714; A61B 17/1675; A61B 17/1635
USPC ....... 606/79, 80, 86 R, 87–89, 96; 623/13.12, 623/13.14
See application file for complete search history.

(56) References Cited

U.S. PATENT DOCUMENTS

| | | | |
|---|---|---|---|
| 4,738,255 A | 4/1988 | Goble et al. | |
| 5,437,675 A * | 8/1995 | Wilson | 606/80 |
| 5,817,095 A | 10/1998 | Smith | |
| 5,919,196 A * | 7/1999 | Bobic et al. | 606/86 R |
| 5,935,134 A | 8/1999 | Pedlick et al. | |
| 6,036,695 A | 3/2000 | Smith | |
| 6,041,485 A | 3/2000 | Pedlick et al. | |
| 7,238,189 B2 * | 7/2007 | Schmieding et al. | 606/80 |
| 7,637,910 B2 * | 12/2009 | Schmieding et al. | 606/80 |
| 7,736,364 B2 * | 6/2010 | Stone | 606/80 |
| 8,070,750 B2 * | 12/2011 | Wenstrom et al. | 606/84 |
| 2004/0092950 A1 * | 5/2004 | Pohjonen et al. | 606/96 |
| 2004/0199166 A1 * | 10/2004 | Schmieding et al. | 606/79 |
| 2005/0070907 A1 * | 3/2005 | Abernathie | 606/80 |
| 2005/0203523 A1 * | 9/2005 | Wenstrom et al. | 606/79 |
| 2006/0015110 A1 * | 1/2006 | Pepper | 606/80 |
| 2007/0093842 A1 * | 4/2007 | Schmieding | 606/80 |
| 2007/0276392 A1 * | 11/2007 | Beyar et al. | 606/80 |
| 2008/0319478 A1 | 12/2008 | Foerster et al. | |
| 2009/0024130 A1 * | 1/2009 | Lombardo | 606/80 |
| 2009/0054928 A1 | 2/2009 | Denham et al. | |

* cited by examiner

*Primary Examiner* — Kevin T Truong
*Assistant Examiner* — Si Ming Ku
(74) *Attorney, Agent, or Firm* — Schwegman Lundberg & Woessner, P.A.

(57) ABSTRACT

A method and tool for forming a hole in a bone. The method includes bringing a bone cutting tool extending along a longitudinal axis into engagement with a cortical portion of the bone. A distal portion of the bone cutting tool is passed into the cortical portion of the bone up to a first predetermined depth to form a first bore. The bone cutting tool is then driven in the axial direction to a second predetermined depth to form a keyway portion in the first bore with a cutting tooth of the bone cutting tool. The bone cutting tool is then rotated about the longitudinal axis to form a second bore in a cancellous portion of the bone. The first bore and the second bore have a shoulder extending therebetween. The bone cutting tool is removed from the hole formed by the first and second bores in the bone.

26 Claims, 14 Drawing Sheets

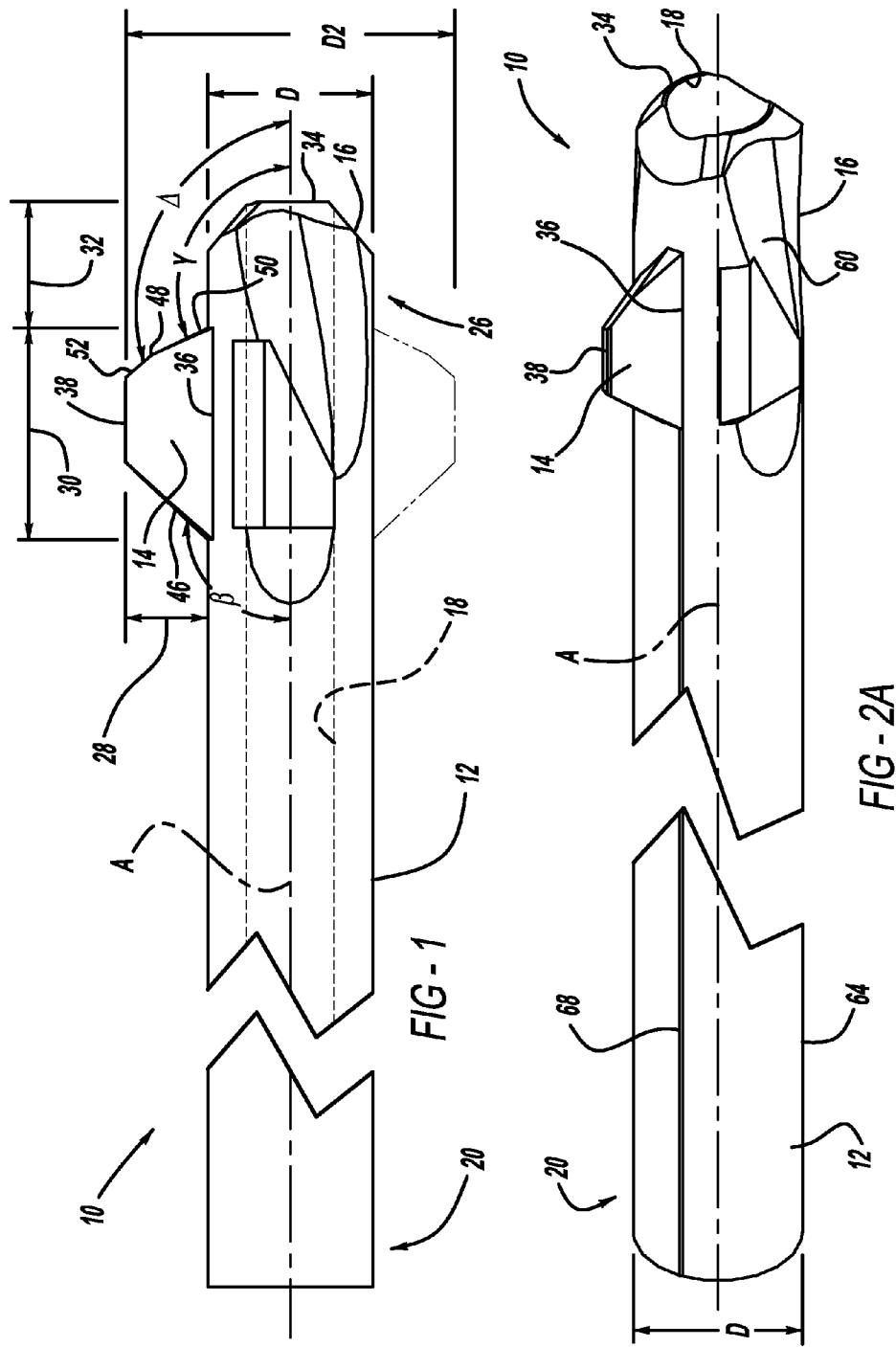

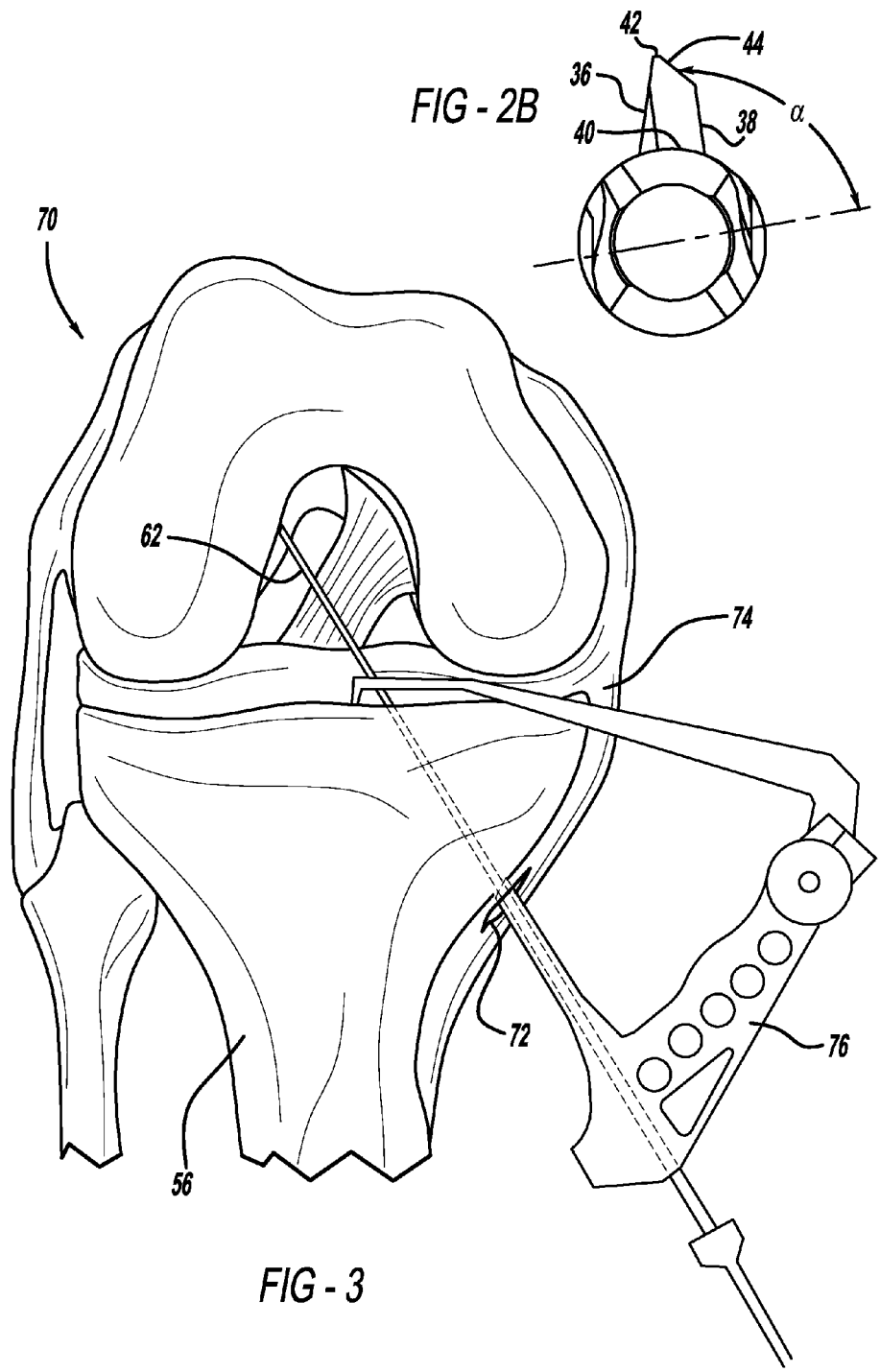

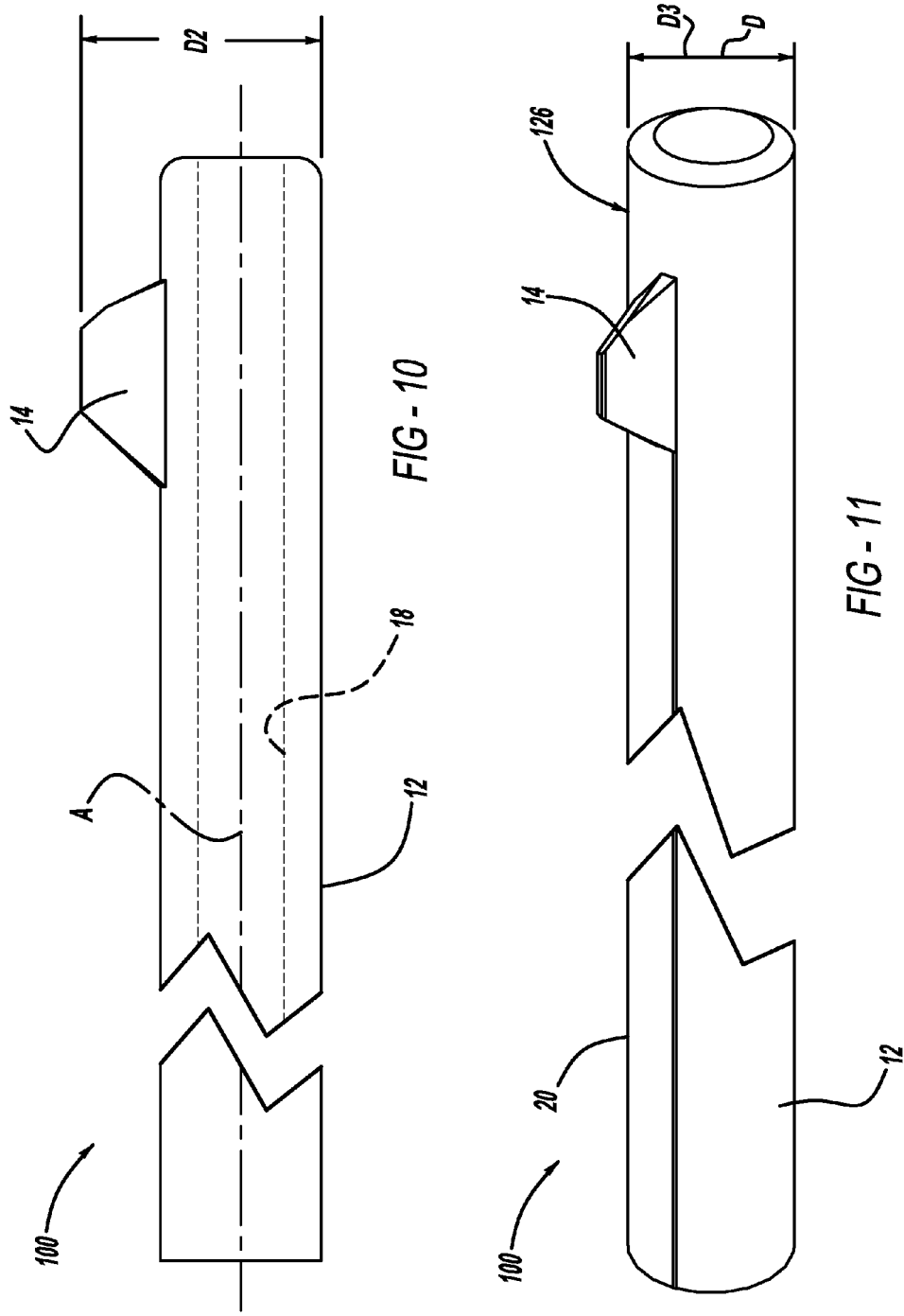

METHOD AND APPARATUS FOR FORMING A HOLE IN BONE DURING A SURGICAL PROCEDURE

FIELD

The present disclosure relates generally to orthopedic procedures; and relates particularly to a method and an apparatus for forming a hole in a bone for tissue fixation.

BACKGROUND

This section provides background information related to the present disclosure which is not necessarily prior art.

In an anatomy, such as a human anatomy, various soft tissue portions are interconnected with various bony portions. For example, a tendon may interconnect a selected muscle group with a selected portion of the anatomy. Similarly, a ligament may interconnect two bony portions. For example, the anterior cruciate ligament (ACL) interconnects a portion of the tibia with a portion of the femur. Although natural and healthy ligaments, tendons, and other selected soft tissues are generally able to support the various portions of the anatomy, injury, age, or other circumstances may cause the weakening or tearing of these various soft tissue portions. In particular, injury or disease may weaken various soft tissue portions, requiring the tissue to be reconnected or replaced with various autografts or xenografts. These various materials may be interconnected with selected portions of the anatomy using various anchoring devices implanted within a bore formed in the bone.

SUMMARY

This section provides a general summary of the disclosure, and is not a comprehensive disclosure of its full scope or all of its features.

In one form, the present disclosure provides a method for forming a hole in a bone. The method includes bringing a bone cutting tool extending along a longitudinal axis into engagement with a cortical portion of the bone. A distal portion of the bone cutting tool is passed into the cortical portion of the bone up to a first predetermined depth to form a first bore. The bone cutting tool is then driven in the axial direction to a second predetermined depth to form a keyway portion in the first bore with a cutting tooth of the bone cutting tool. The bone cutting tool is then rotated about the longitudinal axis to form a second bore in a cancellous portion of the bone. The first bore and the second bore have a shoulder extending therebetween. The bone cutting tool is removed from the hole formed by the first and second bores in the bone.

In another form, the present disclosure provides a method for forming a hole in a bone. The method includes bringing a bone cutting tool into engagement with an outer surface of the bone. A distal portion of the bone cutting tool is then rotated about a longitudinal axis while driving a fluted tip of the bone cutting tool into a cortical portion of the bone up to a first predetermined depth to form a first bore extending from the outer surface of the bone. The bone cutting tool is driven in an axial direction to a second predetermined depth to form a keyway radially extending from the first bore and through the cortical portion of the bone with a cutting tooth of the bone cutting tool. The bone cutting tool is then rotated to form a second bore in a cancellous portion of the bone, the first bore and the second bore having a shoulder extending therebetween. Next a marking line on the bone cutting tool is aligned with the keyway and the bone cutting tool is removed from the hole formed by the first and second bores while the marking line is aligned with the keyway. A repair tissue is then inserted into the second bore with a fixation device positioned relative to the first bore for retaining the repair tissue in the second bore.

In yet another form, the present disclosure provides a bone cutting tool having a shaft portion extending from a proximal end to a distal end along a central longitudinal axis. The shaft portion defines a through bore extending from the proximal end to the distal end of the shaft portion. The through bore is coaxially aligned with the shaft portion. A cutting tooth radially extends from the shaft portion near the distal end. Furthermore, the cutting tooth has a sharpened first edge for axial movement into a cortex of a bone and a sharpened apex for rotational movement through a cancellate of a bone.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a side view of a bone cutting device constructed in accordance with the teachings of the present disclosure;

FIG. 2A is a perspective view of the bone cutting device of FIG. 1;

FIG. 2B is an end view of the bone cutting device of FIG. 1;

FIG. 3 is a perspective view of an aimer in association with a bone of a body;

FIG. 10 is a side view of an alternate bone cutting device constructed in accordance with the teachings of the present disclosure;

FIG. 11 is a perspective view of the bone cutting device of FIG. 10; and

Corresponding reference numerals indicate corresponding parts throughout the several views of the drawings.

DETAILED DESCRIPTION

Figure 4:
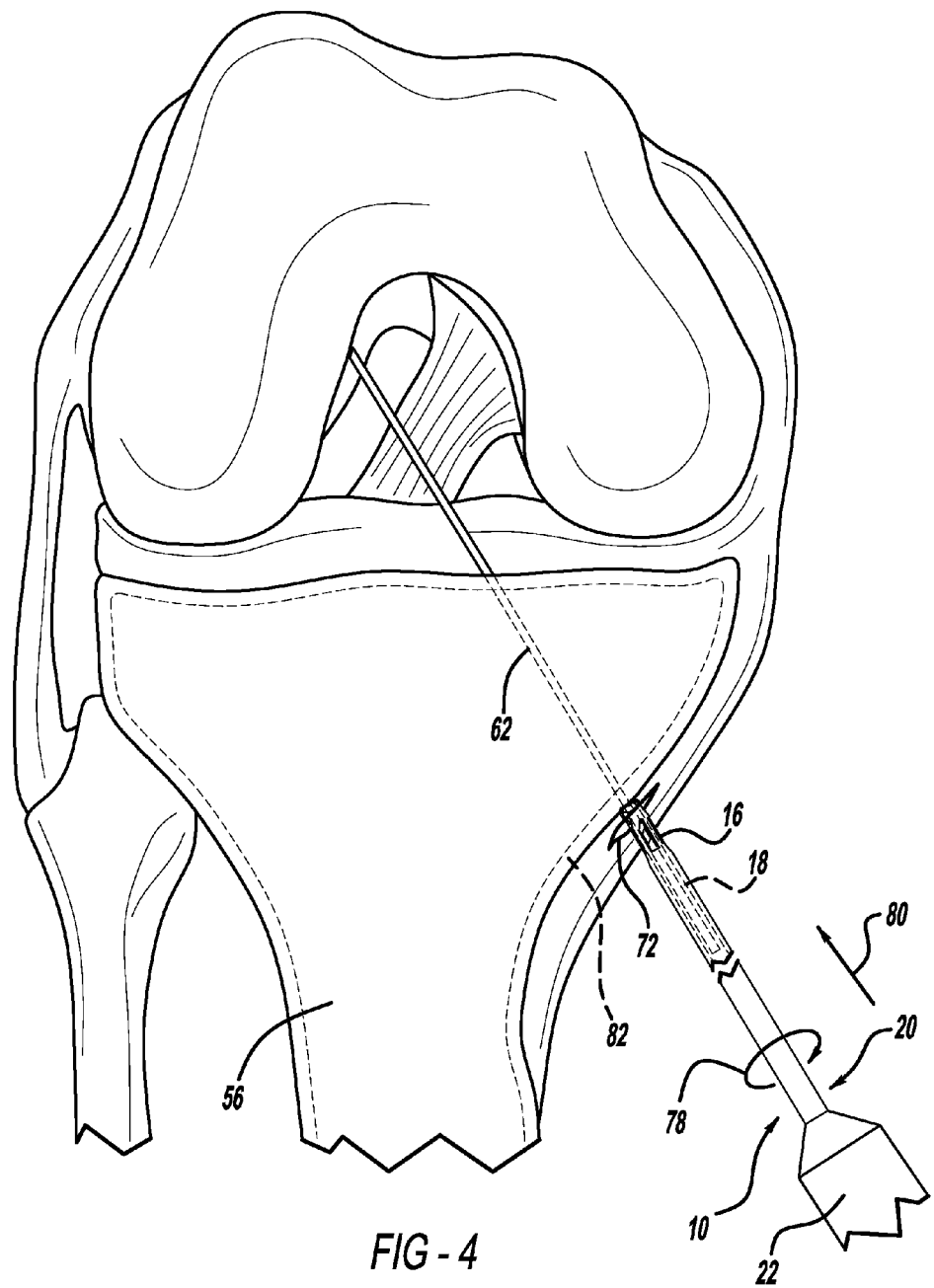
FIG. 4 is a perspective view of the bone cutting device of FIG. 1 in an initial operative position in association with the bone of the body.

The following description of various embodiments is merely exemplary in nature and is not intended to limit the present disclosure, its application, or uses. It should be understood that throughout the drawings, corresponding reference numerals indicate like or corresponding parts and features. With reference to FIGS. 1-14, various methods and apparatuses are disclosed for providing a hole in a bone during an anterior cruciate ligament (ACL) procedure. However, the methods and apparatuses may also be used for a plurality of surgical procedures where a bone hole is required, such as in a hamstring repair, an Achilles tendon allograft, or other soft tissue repair. In addition, although a toggle anchor is shown for the tissue fixation, it will be understood that any securing member may be situated in a bone bore formed by the apparatuses. Furthermore, the replacement of a tendon or a ligament is not necessarily a requirement of the following apparatuses or methods. The apparatuses and methods may also be augmented to provide for various or similar procedures without being outside of the scope of the following description and the appended claims. Therefore, it will be understood that the following discussions are not intended to limit the scope of the present teachings or claims herein.

Referring now to FIGS. 1, 2A, and 2B of the drawings, a cannulated bone cutting tool is generally indicated by reference number 10. The cannulated bone cutting tool 10 is shown to include an elongated body or shaft 12, at least one flag or cutting tooth 14, a fluted end 16, and a longitudinally extending bore 18. The shaft 12 can include a first, proximal end 20 configured for receipt by a driving device. For example, the driving device may be a handle (not shown), a chuck of a power driver 22 (FIG. 4), or a mallet 24 (FIG. 6), as will be described in more detail below. The shaft 12 can also include an opposite second, distal end 26 having the cutting tooth 14 and terminating at the fluted end 16. The shaft 12 extends along an axis, A, and is configured to have a constant diameter, D, over its length (e.g., 4.5 mm). Alternately, the shaft 12 may have a varied diameter so as to form an integral shoulder portion (not shown) at the proximal end 20 for receiving the driving device.

It should be understood that the bone cutting tool 10 may be formed of any rigid material. For example, various biocompatible metals may be used that may be easily formed and sharpened to form the fluted end 16. Various alternatives may also include ceramics and polymers. It should also be understood that only the distal end 26 may be formed from a rigid material. In such a case, the proximal end 20 of the shaft 12 may be formed from any flexible material known in the art and typically used for maneuvering in minimally invasive surgeries (i.e., arthroscopic surgery for replacing an ACL).

The cutting tooth 14 may be coupled to the shaft 12 and extend radially outwardly therefrom by a predetermined distance 28 (e.g., 1-5 mm) and over a predetermined length 30 (e.g., 4-10 mm). The cutting tooth 14 can be formed by machining the distal end 26 of the shaft 12 or otherwise connecting the cutting tooth 14 to the distal end 26 (e.g., welding). The cutting tooth 14 may be located proximally a depth 32 (e.g., 2-10 mm) from a distal most end 34 of the fluted end 16. The depth 32 may correspond to a depth necessary for allowing the bone cutting tool 10 to pierce through cortical bone, while maintaining the cutting tooth 14 against an external surface of the bone, as will be described in more detail below.

Furthermore, the cutting tooth 14 may be generally pyramidal in shape so as to have a pair of opposing faces 36, 38 beginning at a base 40 and tapering towards an apex 42 of the cutting tooth 14. The apex 42 of the cutting tooth 14 may have a faceted surface 44 so as to provide a rotational cutting edge for the cutting tooth 14. For example, the faceted surface 44 may be provided at an angle, $\alpha$, with respect to a plane extending longitudinally through the shaft 12, as best shown in FIG. 2B.

The cutting tooth 14 may also have an angled trailing edge 46 at an angle, $\beta$, with respect to the plane through the shaft 12, and a faceted lead cutting edge 48 having a first, lower portion 50 at an angle, $\gamma$, with respect to the shaft 12, and a second, upper portion 52 at an angle, $\Delta$, with respect to the shaft 12. The angle, $\beta$, of the trailing edge 46 allows for minimal resistance during removal of the bone cutting tool 10 from the bone, while the angles, $\gamma$ and $\Delta$, of the faceted lead cutting edge 48 provide an axial cutting edge for the cutting tooth 14 as the bone cutting tool 10 is being driven axially into bone, as will be described in more detail below. Nevertheless, it will be understood that the cutting tooth 14 may be any appropriate shape, such as generally rectangular and include portions that are fluted to provide an alternative cutting mode for the instrument and to remove the least amount of bone.

Rotation of the cutting tooth 14 (as shown in phantom in FIG. 1) may provide a second diameter, D2, of the cannulated bone cutting tool 10, which is larger than the first diameter, D, of the shaft 12. Furthermore, the distance 28 and length 30 can be varied to provide an appropriately dimensioned hole 54 in a bone (e.g., tibia 56) for receipt of a repair tissue 58 (see FIG. 9), as will be described in more detail below. Additionally, the depth 32 of the cutting tooth 14 from the distal most end 34 may vary for establishing the location of the bone hole 54 in portions of the body where the thickness of the cortex varies. In other words, as the depth 32 is a depth designed to penetrate greater than the cortical depth, a plurality of tools may be provided to accommodate different cortical depths. This cortical depth may be determined by x-ray or other previously obtained knowledge.

Bone cutting can also be initiated through the fluted end 16. The fluted end 16 can include a plurality of cutting edges or flutes 60. In the exemplary configuration shown, the cannulated bone cutting tool 10 includes two flutes 60, but any number of flutes 60 is contemplated. The flutes 60 can extend from the distal most end 34 of the shaft 12 so as to provide a path for removed bone material to exit during use.

The cannulated bone cutting tool 10 can also include the longitudinal bore 18 extending from the proximal end 20 to the distal end 26 of the shaft 12 for receipt of a guide wire 62 (FIG. 3). The longitudinal bore 18 has an axis coinciding with the axis, A. Furthermore, the longitudinal bore 18 may be open at the distal most end 34 and appropriately sized (e.g., 2.5 mm) in order to allow the guide wire 62 to pass therethrough, as will be described in more detail below.

Figure 8:
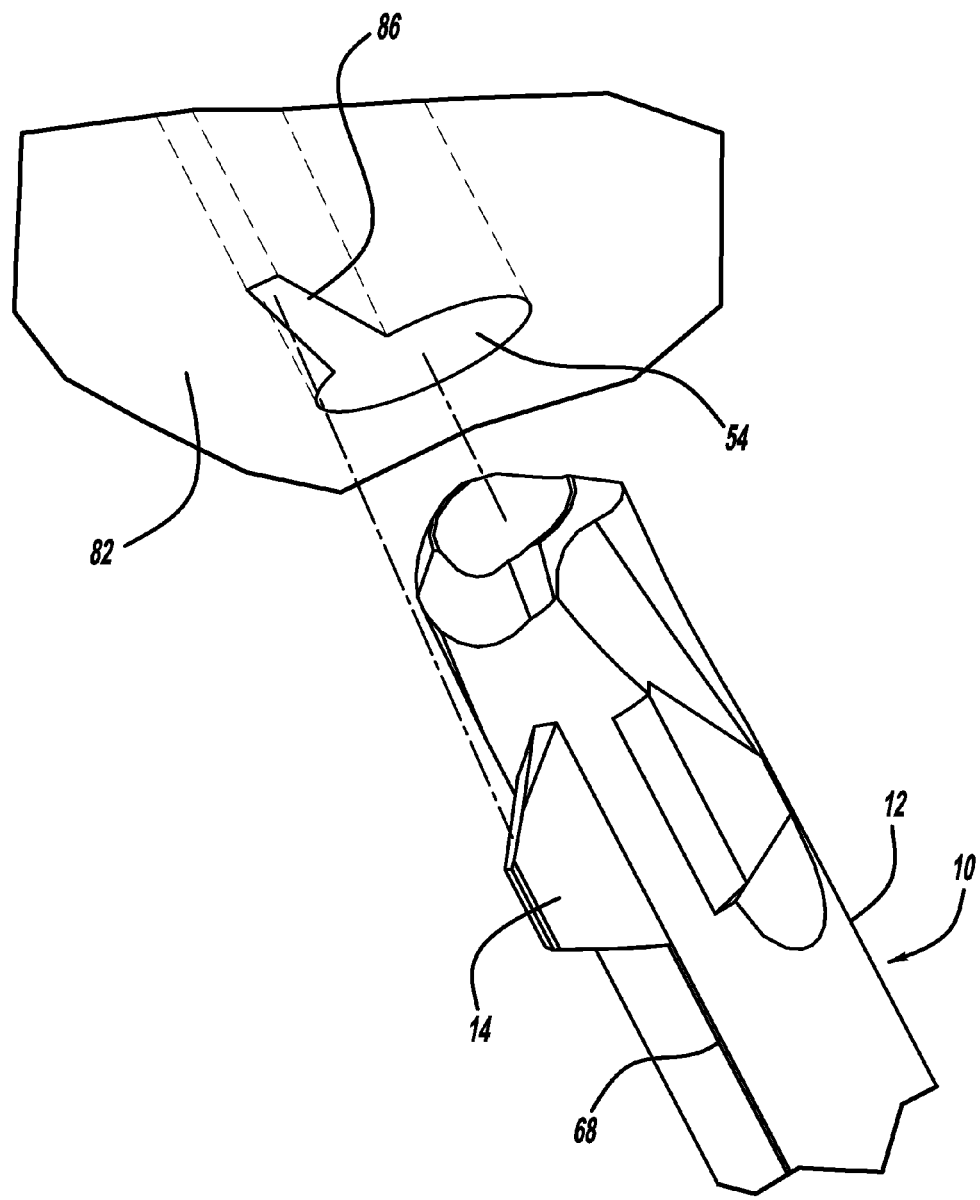
FIG. 8 is a perspective view of the bone cutting device of FIG. 1 being removed from the bone of the body.

An exterior surface 64 of the shaft 12 may include a plurality of demarcations 66 (FIG. 6A) indicating an appropriate scale. For example, the markings 66 may be included at approximately 10 mm intervals extending axially such that markings at 10, 20, 30, 40, etc mm are provided on the exterior surface 64 of the shaft 12. A user may view the markings 66 on the exterior surface 64 of the shaft 12 to determine the depth of the bone cutting tool 10 within the selected bone. Furthermore, an axial line 68 may be etched or lasered onto the exterior surface 64 as to align with the cutting tooth 14. The laser line 68 may extend from the base 40 of the cutting tooth 14 to the proximal end 20 of the shaft 12 for assisting a surgeon in aligning and removing the bone cutting tool 10 from the bone after surgery (FIG. 8).

Referring now to FIGS. 3-9, the foregoing cannulated bone cutting tool 10 may be used to form a blind bore, concavity, or the bone hole 54 during an anterior cruciate ligament (ACL) reconstruction. As discussed above, the ACL reconstruction is simply exemplary as the general process described herein can be used to provide the bone hole 54 in any selected portion of the anatomy, such as in a femur, humerus, or any other appropriate bone portion. In addition, the bone hole 54 may be formed for any selected procedure and not simply an ACL reconstruction. However, this bone cutting tool 10 provides additional benefits in the ACL reconstruction, as it provides an enlarged hole within the tibia 56 for receipt of the repair tissue 58, but still only allows a minimal amount of cortex removed (e.g., for ease in healing and for reduced pain to a patient).

With particular reference to FIG. 3, a selected knee joint 70 can be first prepared for the ACL procedure. First, an incision 72 may be formed in a soft tissue 74 surrounding the knee joint 70. After the incision 72 is formed, an aimer 76 may be used to guide the guide wire 62 through a selected portion of the tibia 56. Appropriate aimers 76 are generally known and need not be described in detail herein. Also, other techniques for placing the guide wire 62 in the tibia 56 are also generally known and not described in detail herein. For example, such a device and method is described in U.S. Pat. No. 7,736,364, Stone, issued Jun. 15, 2010, and is incorporated by reference in its entirety herein. It will also be understood that the incision 72 may be any appropriate size, but is generally between about 1 cm to about 10 cm. Therefore, the procedure may be augmented with an arthroscope (not shown) that is either passed through the incision 72 or other appropriate incisions.

Referring now to FIG. 4, the longitudinal bore 18 of the cannulated bone cutting tool 10 can be passed over the guide wire 62 to guide the bone cutting tool 10 as it is brought into engagement with the tibia 56. In certain embodiments, the driver 22 may be engaged with the proximal end 20 of the bone cutting tool 10 before passing over the guide wire 62. However, the driver 22 may also be fixed to the proximal end 20 after the bone cutting tool 10 is passed through the incision 72 and placed into alignment with the tibia 56. In either case, the driver 22 may be any device that imparts both a rotational (as shown by arrow 78) and an axial force (as shown by arrow 80) to the bone cutting tool 10. The fluted end 16 of the bone cutting tool 10 is first positioned relative an anterior cortical portion 82 of the tibia 56. Accordingly, a reduced size hole may be formed through the cortical portion 82 of the tibia 56.

Figure 5:
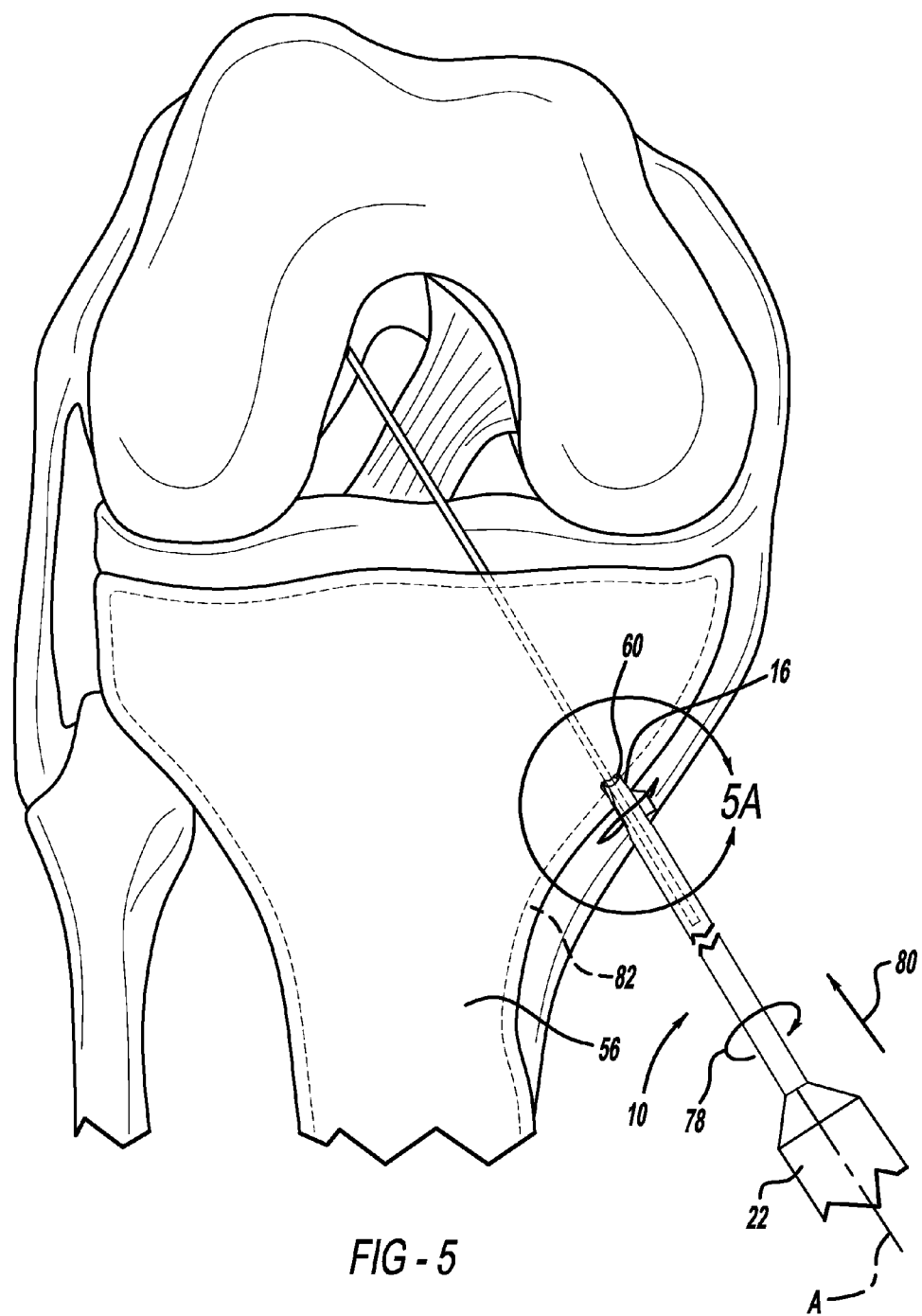
FIGS. 5 through 7 are perspective views of the bone cutting device of FIG. 1 in intermediate operative positions with respect to the bone of the body.
Figure 5A:
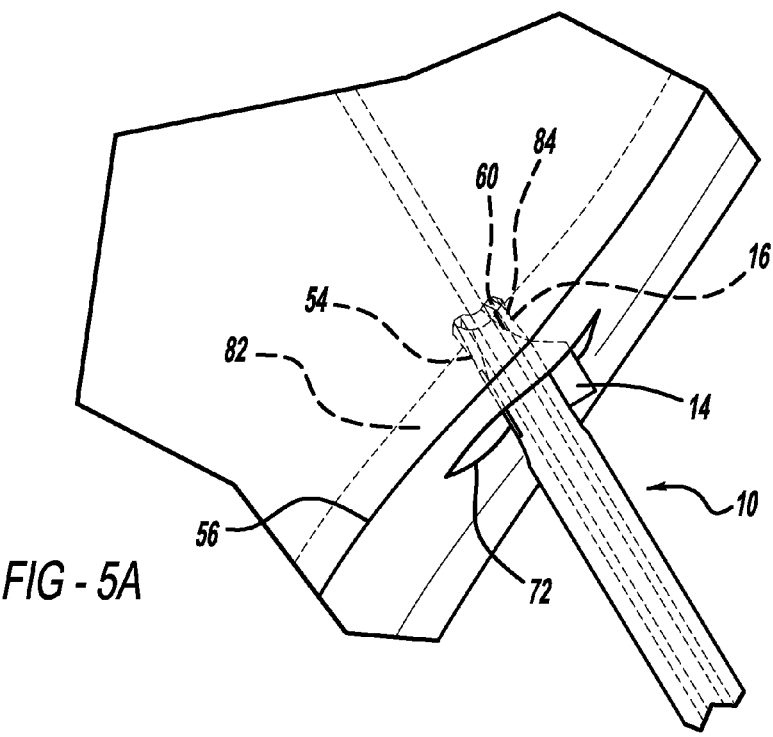

With reference now to FIGS. 5 and 5A, the bone cutting tool 10 may now be rotated around longitudinal axis, A, in the rotational direction 78 by manipulation of the driver 22. The driver 22 may impart the rotational and axial forces 78, 80 so as to gradually pierce the flutes 60 of the fluted end 16 into and through the cortical portion 82 of the tibia 56. This inward rotation establishes a first cylindrical portion 84 of the bone hole 54 having a diameter correspondingly sized with the diameter, D, of the shaft 12. The driver 22 continues to rotate the bone cutting tool 10 and remove material from the bone hole 54 until the cutting tooth 14 is aligned with the outer anterior cortex of the tibia 56. In other words, the rotational and axial movement of the driver 22 moves the flutes 60 through the cortical portion 82 of the tibia 56, which brings the cutting tooth 14 into alignment with the outer surface of the tibial cortex.

Figure 6A:
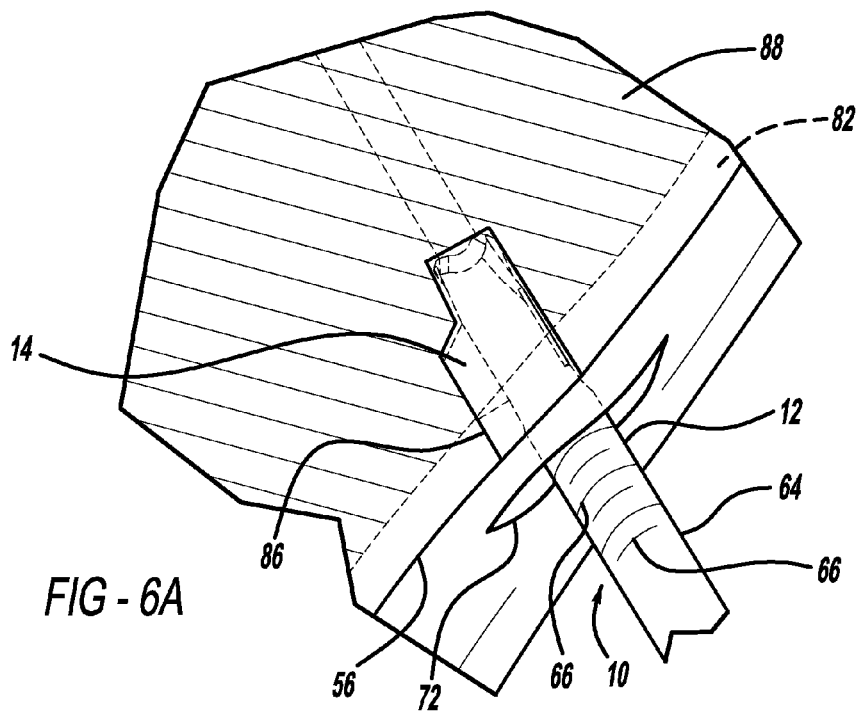
Figure 6:
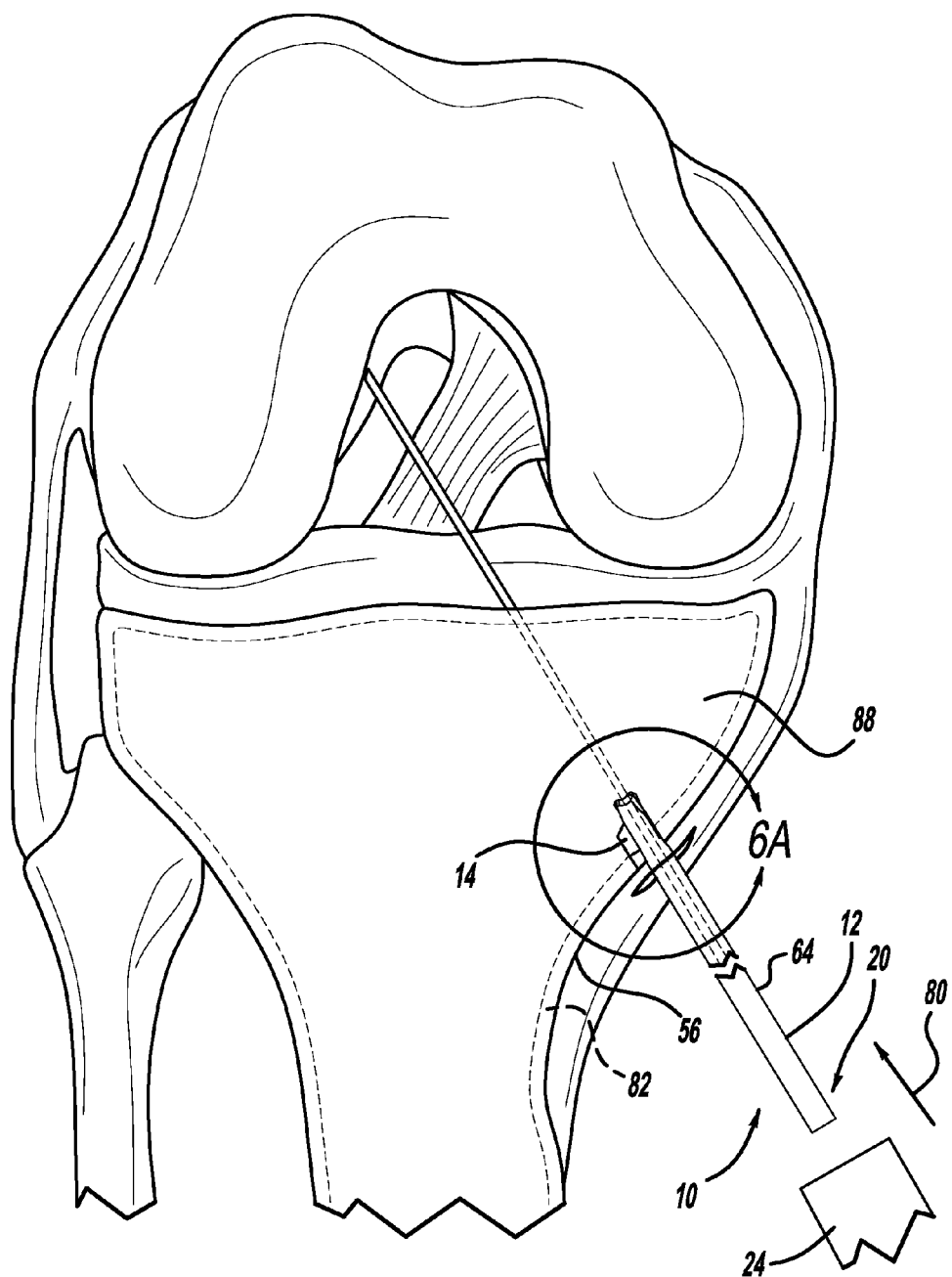

Referring now to FIGS. 6 and 6A, the driver 22 may be decoupled from the bone cutting tool 10, while keeping the bone cutting tool 10 aligned with the tibia 56. The mallet 24, or any other appropriate instrument, may then be used to strike the proximal end 20 of the shaft 12 in the axial direction 80. The bone cutting tool 10 may be struck several times to non-rotationally drive the lead cutting edge 48 of the cutting tooth 14 axially into and through the cortical portion 82 of the tibia 56 in order to create a keyway 86.

As discussed above, the markings 66 on the exterior surface 64 of the shaft 12 may be used to determine the depth to which the bone cutting tool 10 has penetrated the tibia 56. The markings 66 may be viewed either through the incision 72 or through a selected arthroscope or other viewing instrument. After the bone cutting tool 10 has passed the selected distance into the tibia 56 (e.g., the cutting tooth 14 is completely within a cancellous portion 88 of the tibia 56), the driver 22 may be reattached to the bone cutting tool 10.

Figure 7:
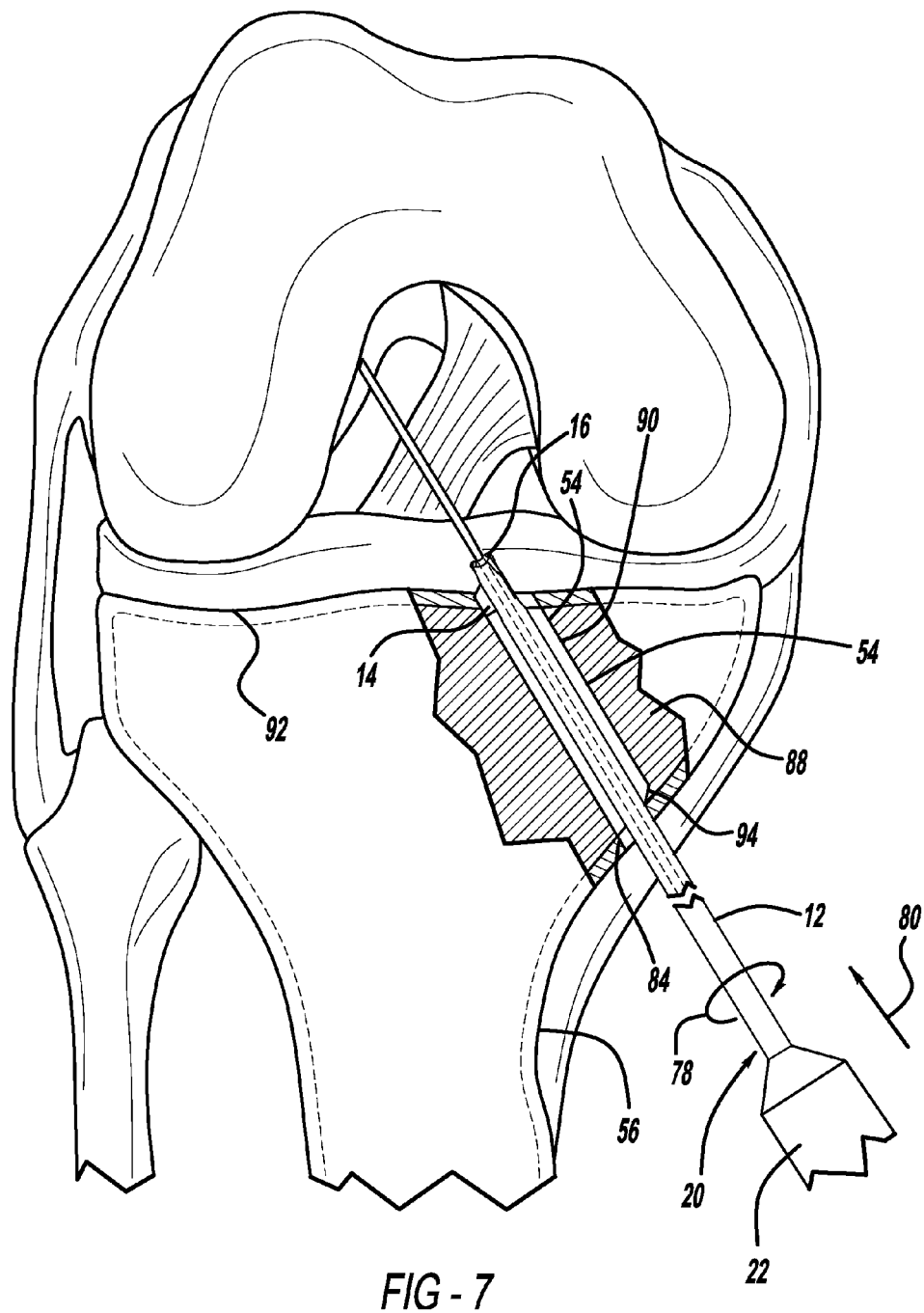

After reattachment of the driver 22 as shown in FIG. 7, the fluted end 16 and the cutting tooth 14 of the bone cutting tool 10 are positioned relative the cancellous portion 88 of the tibia 56. The driver 22 may again impart the rotational and axial forces 78, 80 to the bone cutting tool 10 through the proximal end 20 of the shaft 12. The driver 22 rotationally drives the flutes 60 of the fluted end 16 and the cutting tooth 14 of the bone cutting tool 10 through the cancellous portion 88 of the tibia 56 to establish a second portion 90 of the bone hole 54. Notably, the second portion 90 of the bone hole 54 may have a diameter correspondingly sized with the diameter, D2, of the rotational cutting tooth 14. The driver 22 continues to rotate the bone cutting tool 10 and remove material from the bone hole 54 until the bone cutting tool 10 rotates and extends through a tibial plateau 92 of the tibia 56. In this way, the cortical portion 82 of the tibia 56 has a minimal amount of bone material removed, while the second portion 90 is enlarged for receipt of the repair tissue 58 within the cancellous portion 88 of the tibia 56. It should be understood, however, that the cortex at the tibial plateau 92 is bored to a similar diameter as the second portion 90.

In order to remove the bone cutting tool 10 from the tibia 56 without removing further amounts of the cortical portion 82, the laser line 68 on the shaft 12 is rotated into alignment with the keyway 86 or slot formed into the cortex (FIG. 8). The bone cutting tool 10 may then be axially removed from the first and second portions 84, 90 of the bone hole 54. In this way, the bone hole 54 may have a minimal amount of bone material removed from the cortical portion 82 of the tibia 56, allowing the surgeon to prepare a socket for a graft without violating the tibial wall with a large diameter hole. As previously discussed, the first portion 84 of the bone hole 54 is correspondingly sized with the diameter, D2, of the rotational cutting tooth 14 and the second portion 90 is correspondingly sized with the diameter, D, of the shaft 12 creating a shoulder 94 within the bone hole 54.

Figure 9:
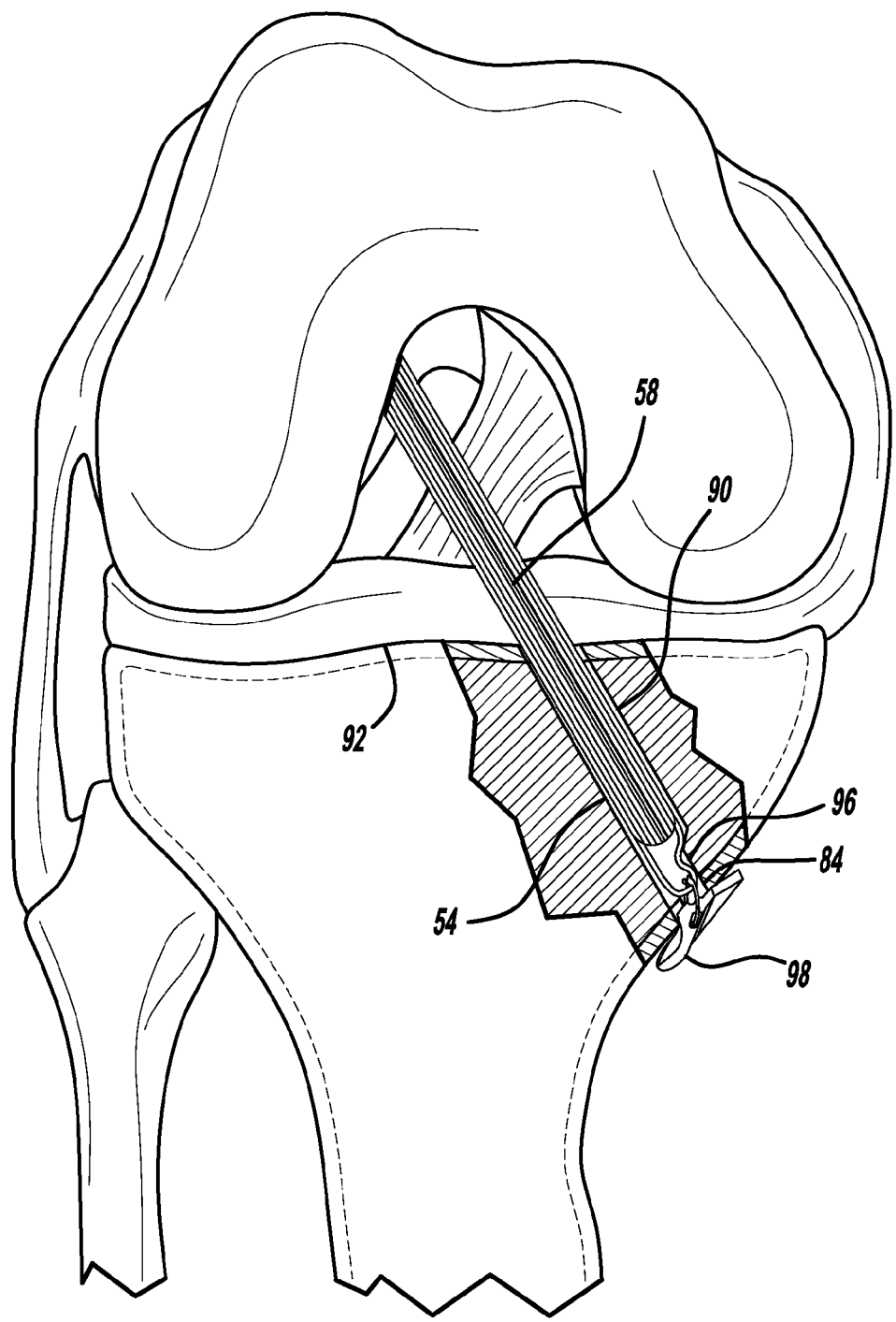
FIG. 9 is a cross-sectional view of a bone socket established by the bone cutting device of FIG. 1 incorporating a tissue.

With reference now to FIG. 9, the bone hole 54 is sized to receive a tissue fixation device, such as a toggle anchor 96. It should be understood that while one exemplary tissue fixation device is described herein, other tissue anchoring devices are contemplated. For example, soft anchors having a single suture extending therethrough or rigid anchors may be used. The toggle anchor 96 can be preassembled to include a looped configuration joined with the repair tissue 58, as described in U.S. Patent Publication No. 2009/0054928, Denham et al., published Feb. 26, 2009, and incorporated herein by reference in its entirety. In one example as shown herein, the toggle anchor 96 may be passed through the tibial plateau 92 into the first portion 84 of the bone hole 54. A toggle 98 may extend through the second portion 90 of the bone hole 54 so as to engage the outer anterior cortical portion 82 of the tibia 56. In this way, the toggle 98 may be maintained outside the second portion 90 of the bone hole 54, while the repair tissue 58 is drawn into the first portion 84 of the bone hole 54.

With reference now to FIGS. 10 and 11, another exemplary bone cutting tool 100 is provided. The bone cutting tool 100 is similar to the bone cutting tool 10, as the bone cutting tool 100 is also operable for preparing the tibia 56 for receipt of the repair tissue 58. Because many features of the bone cutting tool 100 are similar to those described with reference to the cannulated bone cutting tool 10, a detailed description of these elements is forgone. Furthermore, like reference numerals are used to describe like elements.

The bone cutting tool 100 is shown to include the elongated shaft 12, the cutting tooth 14, and the longitudinally extending bore 18. The shaft 12 may be configured for receipt of the driving device (e.g., driver 22, mallet 24) at the proximal end 20 and have the cutting tooth 14 at a distal end 126, as previously described with respect to the bone cutting tool 10. Furthermore, the bore 18 may also extend through the distal end 126 of the shaft 12 for receipt of the guide wire 62 (FIG. 3). The bone cutting tool 100, however, omits the flutes 60 at the distal end 126. In particular, the distal end 126 has a diameter, D3, that corresponds to the diameter, D, of the shaft 12. As such, the first portion 84 of the bone hole 54 may be pre-drilled for receipt of the bone cutting tool 100 in the cortical portion 82 of the tibia 56 on impact.

In particular, after placement of the guide wire 62 as shown in FIG. 3, a cannulated drill bit (not shown) may be placed over the guide wire 62 and rotated to pass through the cortical portion 82 of the tibia 56. The cortical portion 82 removed may have a diameter equivalent to the shaft 12 of the bone cutting tool 100. After removal of the cortical portion 82, the drill bit is removed and replaced with the bone cutting tool 100.

Figure 12:
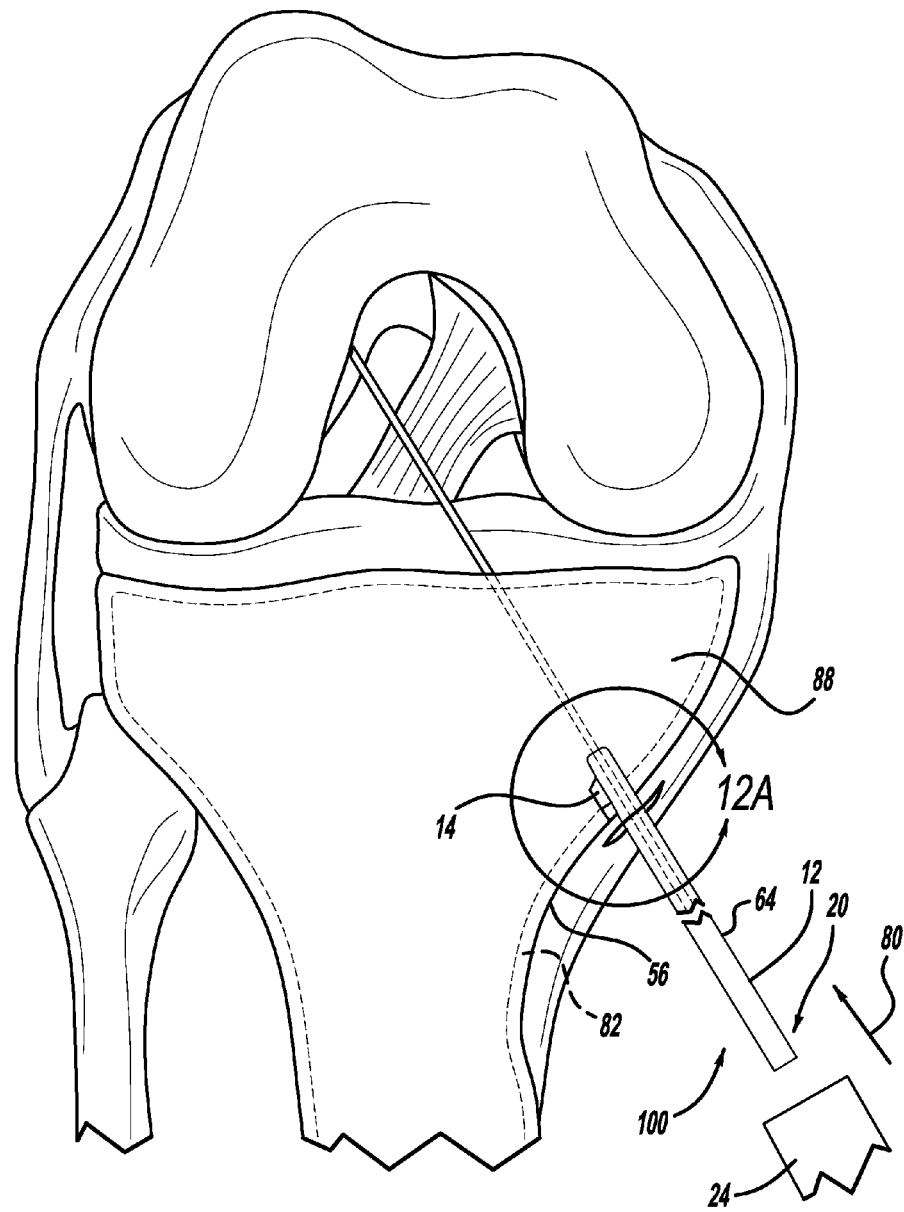
FIGS. 12 through 14 are perspective views of the bone cutting device of FIG. 10 in intermediate operative positions with respect to the bone of the body.
Figure 12A:
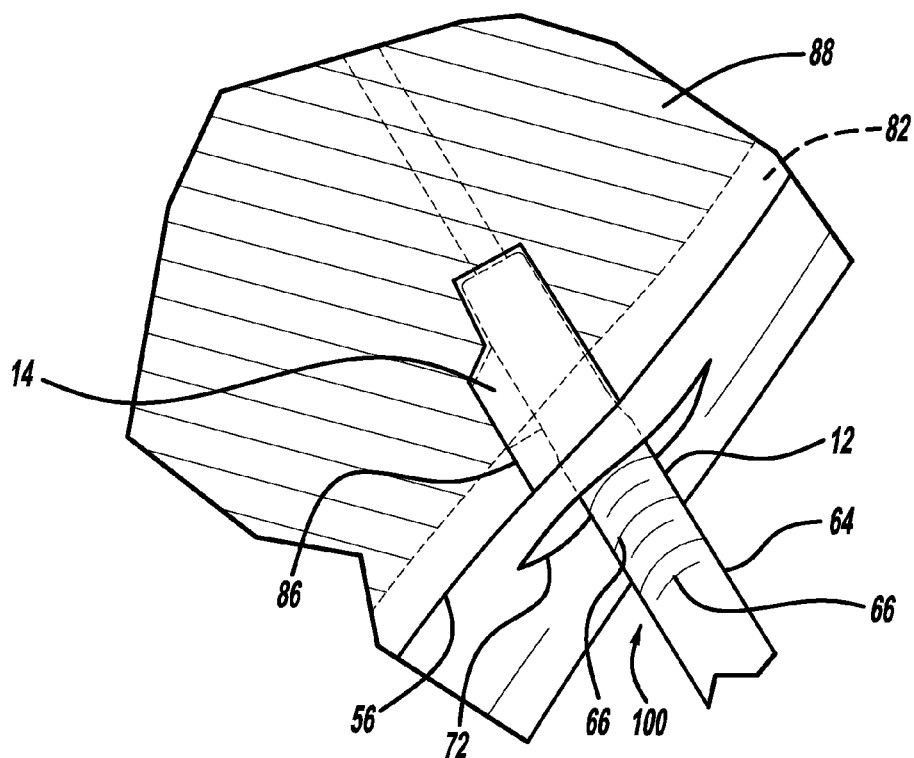

With reference now to FIGS. 12 and 12A, the mallet 24 may then be used to strike the proximal end 20 of the shaft 12 to drive the bone cutting tool 100 and, in particular, the lead cutting edge 48 of the cutting tooth 14 into and through the cortical portion 82 of the tibia 56 to the selected depth completely within the cancellous portion 88 of the tibia 56. In the process, the keyway 86 or slot is formed.

Figure 13:
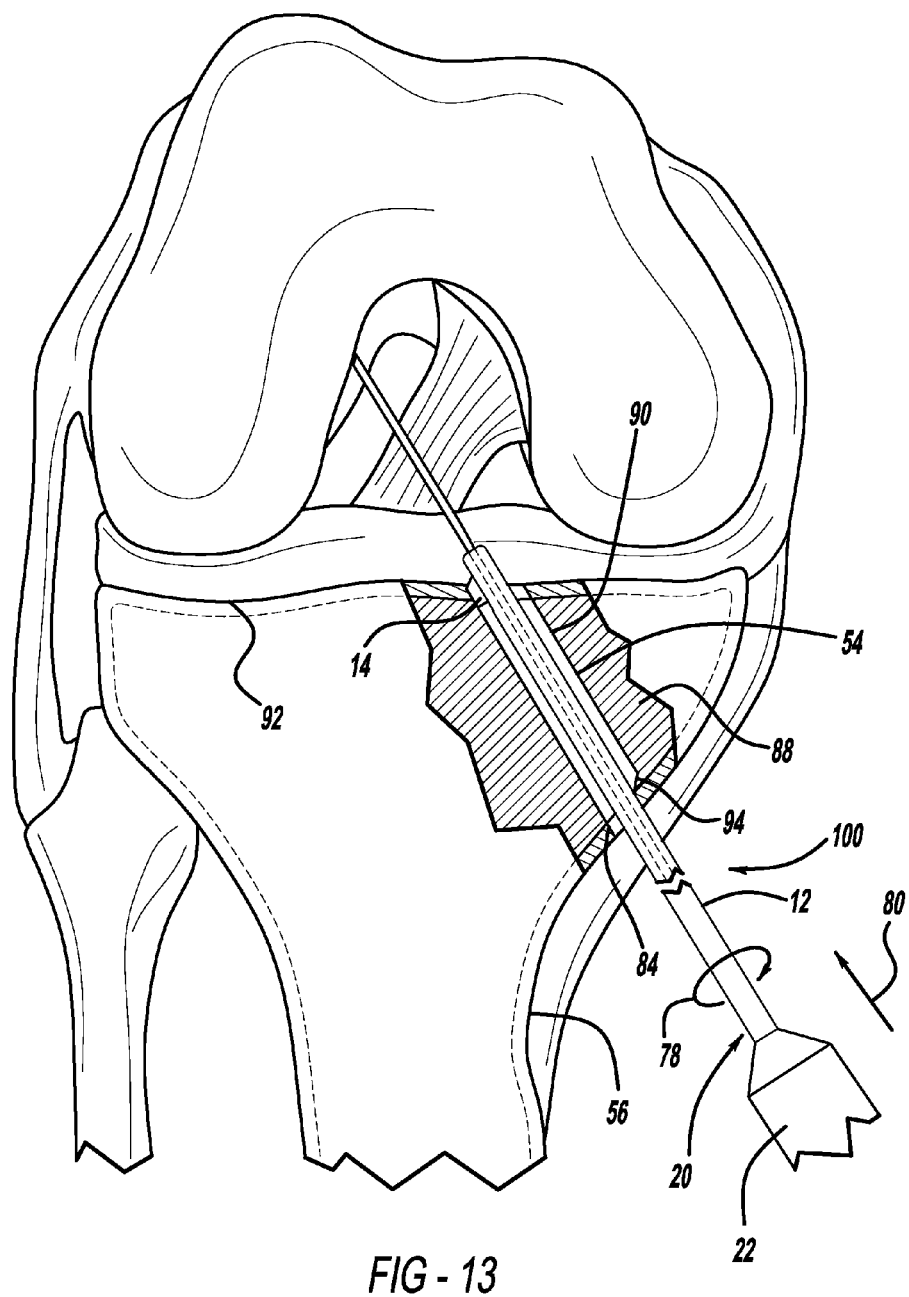
Figure 14:
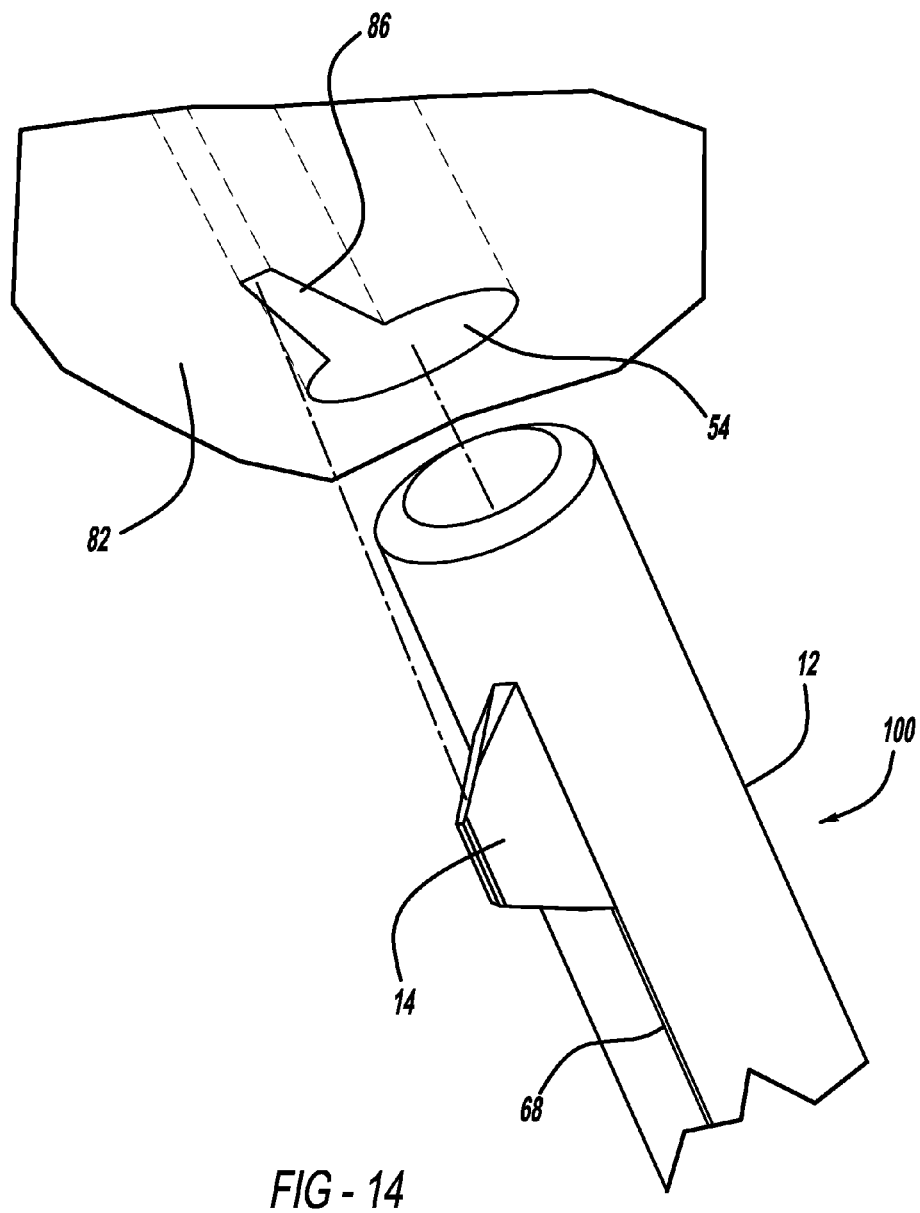

The driver 22 may then be attached to the bone cutting tool 100 for imparting the rotational and axial forces 78, 80 to the bone cutting tool 100 through the proximal end 20 of the shaft 12, as shown in FIG. 13. The driver 22 rotationally drives the cutting tooth 14 of the bone cutting tool 100 through the cancellous portion 88 of the tibia 56 to establish the second portion 90 of the bone hole 54 until the bone cutting tool 100 extends through the tibial plateau 92 of the tibia 56. The laser line 68 on the shaft 12 of bone cutting tool 100 is then rotated into alignment with the keyway 86, for removal therefrom (FIG. 14). As previously discussed, the first portion 84 of the bone hole 54 is correspondingly sized with the diameter, D2, of the rotational cutting tooth 14 and the second portion 90 is correspondingly sized with the diameter, D3, of the distal end 126 creating the shoulder 94 within the bone hole 54.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for forming a hole in a bone, the method comprising:
    bringing a bone cutting tool that extends along a longitudinal axis into engagement with a cortical portion of the bone, the bone cutting tool having a cutting tooth spaced a distance away from a distal-most end of the cutting tool;
    passing a distal portion of the bone cutting tool into the cortical portion of the bone up to a first predetermined depth to form a first bore;
    driving without rotating the bone cutting tool in an axial direction to a second predetermined depth to form an elongated keyway slot extending radially from and along a longitudinal portion of the first bore with the cutting tooth of the bone cutting tool;
    rotating the bone cutting tool about the longitudinal axis to form a second bore deeper than the first bore in a cancellous portion of the bone, the first bore and the second bore having a shoulder extending therebetween; and
    removing the bone cutting tool from the hole formed by the first and second bores in the bone.

2. The method of claim 1, further comprising:
    inserting a repair tissue into the second bore; and
    positioning a fixation device through the first bore to retain the repair tissue in the second bore.

3. The method of claim 2, wherein the bone cutting tool is brought into engagement with an anterior cortical portion of a tibia to form the hole in the tibia.

4. The method of claim 3, wherein inserting the repair tissue includes inserting an anterior cruciate ligament graft into the hole formed in the tibia.

5. The method of claim 1, wherein passing the distal portion of the bone cutting tool into the cortical portion of the bone further includes:
    rotating the bone cutting tool about the longitudinal axis while driving a fluted tip of the bone cutting tool through the cortical portion of the bone to the cancellous portion of the bone to form the first bore, where the first predetermined depth is greater than the depth of the cortical portion of the bone.

6. The method of claim 1, wherein rotating the bone cutting tool about the longitudinal axis is performed with a driver attached to a proximal end of the bone cutting tool, the method further comprising:
    removing the driver from the proximal end of the bone cutting tool;
    striking the proximal end of the bone cutting tool to drive the bone cutting tool in the axial direction to the second predetermined depth; and
    reattaching the driver to the proximal end of the bone cutting tool for rotating the bone cutting tool about the longitudinal axis to form the second bore through the cancellous portion of the bone.

7. The method of claim 1, further comprising:
    aligning a line on the bone cutting tool that extends from the cutting tooth with the keyway slot before removing the bone cutting tool from the bone; and
    removing the bone cutting tool from the hole while the line is aligned along the keyway slot.

8. The method of claim 1, wherein passing the distal portion of the bone cutting tool into the cortical portion of the bone further includes:
    pre-drilling the cortical portion of the bone up to the first predetermined depth for axially receiving the distal portion of the bone cutting tool.

9. The method of claim 1, wherein forming the first bore and the second bore includes forming the first bore having a first diameter and forming the second bore having a second diameter, where the first diameter is less than the second diameter.

10. The method of claim 1, further comprising:
    guiding the bone cutting tool over a guide wire positioned in the bone.

11. A method for forming a hole in a bone, the method comprising:
    bringing a bone cutting tool into engagement with an outer surface of the bone, the bone cutting tool having a distal portion with a fluted tip and a cutting tooth proximally to the fluted tip and spaced a distance away from a distal-most end of the fluted tip;

rotating the distal portion of the bone cutting tool about a longitudinal axis while driving the fluted tip of the bone cutting tool into a cortical portion of the bone up to a first predetermined depth to form a first bore extending from the outer surface of the bone;

driving without rotating the bone cutting tool in an axial direction to a second predetermined depth to form an elongated keyway slot radially extending from the first bore and through the cortical portion of the bone and along a longitudinal portion of the first bore with the cutting tooth of the bone cutting tool;

rotating the bone cutting tool to form a second bore in a cancellous portion of the bone, the first bore and the second bore having a shoulder extending therebetween;

rotationally aligning a marking line on the bone cutting tool with the keyway slot; and removing the bone cutting tool from the hole formed by the first and second bores while the marking line is aligned with the keyway slot.

12. The method of claim 11, further comprising:
inserting a repair tissue into the second bore; and
positioning a fixation device relative to the first bore to retain the repair tissue in the second bore.

13. The method of claim 11, wherein rotating the bone cutting tool about the longitudinal axis is performed with a driver attached to a proximal end of the bone cutting tool, the method further comprising:
removing the driver from the proximal end of the bone cutting tool; and
striking the proximal end of the bone cutting tool to drive the bone cutting tool in the axial direction to the second predetermined depth; and
reattaching the driver to the proximal end of the bone cutting tool for rotating the bone cutting tool about the longitudinal axis to form the second bore through the cancellous portion of the bone.

14. The method of claim 11, wherein the first predetermined depth is greater than the depth of the cortical portion of the bone.

15. The method of claim 11, further comprising:
positioning a guide wire within the bone; and
guiding the bone cutting tool over the guide wire before bringing the bone cutting tool into engagement with the outer surface of the bone.

16. The method of claim 11, wherein the bone cutting tool is brought into engagement with an anterior cortical portion of a tibia to form the hole in the tibia.

17. The method of claim 16, wherein inserting the repair tissue includes inserting an anterior cruciate ligament graft into the hole formed in the tibia.

18. The method of claim 11, wherein forming the first bore and the second bore includes forming the first bore having a first diameter and forming the second bore having a second diameter, where the first diameter is less than the second diameter.

19. A method for forming a hole in a bone, the method comprising:
bringing a bone cutting tool into engagement with an outer surface of the bone, the bone cutting tool having a distal portion with a fluted tip and a cutting tooth proximally to the fluted tip and spaced a distance away from a distal-most end of the fluted tip;

rotating the distal portion of the bone cutting tool about a longitudinal axis while driving the fluted tip of the bone cutting tool into a cortical portion of the bone up to a first predetermined depth to form a first bore extending from the outer surface of the bone;

driving without rotating the bone cutting tool in an axial direction to a second predetermined depth to form an elongated keyway slot radially extending from the first bore and through the cortical portion of the bone and along a longitudinal portion of the first bore with the cutting tooth of the bone cutting tool; and rotating the bone cutting tool to form a second bore in a cancellous portion of the bone, the first bore and the second bore having a shoulder extending therebetween, wherein the second bore is distal to the first bore in relation to the outer surface of the bone.

20. The method of claim 19, further comprising:
aligning a marking line on the bone cutting tool with the keyway slot; and
removing the bone cutting tool from the hole formed by the first and second bores while the marking line is aligned with the keyway slot.

21. The method of claim 19, further comprising:
inserting a repair tissue into the second bore; and
positioning a fixation device relative to the first bore to retain the repair tissue in the second bore.

22. The method of claim 21, wherein inserting the repair tissue includes inserting an anterior cruciate ligament graft into the hole formed in the tibia.

23. The method of claim 19, further comprising:
positioning a guide wire within the bone; and
guiding the bone cutting tool over the guide wire before bringing the bone cutting tool into engagement with the outer surface of the bone.

24. The method of claim 19, wherein the bone cutting tool is brought into engagement with an anterior cortical portion of a tibia to form the hole in the tibia.

25. The method of claim 19, wherein forming the first bore and the second bore includes forming the first bore having a first diameter and forming the second bore having a second diameter, where the first diameter is less than the second diameter.

26. The method of claim 19, wherein driving without rotating the bone cutting tool in an axial direction to a second predetermined depth includes striking a proximal end of the bone cutting tool to drive the bone cutting tool in the axial direction to the second predetermined depth.

* * * * *